United States Patent
Ohashi

(10) Patent No.: US 11,589,778 B2
(45) Date of Patent: Feb. 28, 2023

(54) BODY SIZE ESTIMATION APPARATUS, BODY SIZE ESTIMATION METHOD, AND PROGRAM

(71) Applicant: SONY INTERACTIVE ENTERTAINMENT INC., Tokyo (JP)

(72) Inventor: Yoshinori Ohashi, Tokyo (JP)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 96 days.

(21) Appl. No.: 16/978,021

(22) PCT Filed: Mar. 16, 2018

(86) PCT No.: PCT/JP2018/010459
§ 371 (c)(1),
(2) Date: Sep. 3, 2020

(87) PCT Pub. No.: WO2019/176090
PCT Pub. Date: Sep. 19, 2019

(65) Prior Publication Data
US 2020/0405185 A1    Dec. 31, 2020

(51) Int. Cl.
*A61B 5/107* (2006.01)
*A63F 13/212* (2014.01)
(Continued)

(52) U.S. Cl.
CPC .......... *A61B 5/1072* (2013.01); *A63F 13/212* (2014.09); *G01B 21/02* (2013.01); *G06T 7/75* (2017.01); *G06T 2207/30196* (2013.01)

(58) Field of Classification Search
None
See application file for complete search history.

(56) References Cited

U.S. PATENT DOCUMENTS

| | | | |
|---|---|---|---|
| 2009/0193675 A1* | 8/2009 | Sieber | G01B 3/1004 33/759 |
| 2015/0153158 A1* | 6/2015 | Tsao | G01S 17/08 356/634 |
| 2015/0154453 A1* | 6/2015 | Wilf | G06V 10/46 382/103 |

FOREIGN PATENT DOCUMENTS

| | | | |
|---|---|---|---|
| JP | 2002352231 A | 12/2002 | |
| JP | 2007069303 A | 3/2007 | |

(Continued)

OTHER PUBLICATIONS

International Preliminary Report on Patentability dated Oct. 1, 2020, from the corresponding PCT/JP2018/010459, 11 sheets.

(Continued)

*Primary Examiner* — Raul J Rios Russo
*Assistant Examiner* — Carl F. R. Tchatchouang
(74) *Attorney, Agent, or Firm* — Katten Muchin Rosenman LLP

(57) ABSTRACT

Provided are a body size estimation apparatus, a body size estimation method, and a program that enable the estimation of the body size of a user even when the user has not taken a T-pose in advance. A body size data storage unit (50) stores body size data indicating a body size of a user. A posture data acquisition unit (52) acquires position data indicating positions of a plurality of body parts away from each other of the user. A body size estimation unit (54) estimates a body size of the user based on positions of two or more body parts indicated by the position data. A body size update unit (56) updates, in a case where the estimated body size is larger than the body size indicated by the body size data stored in the body size data storage unit (50), the body size indicated by the body size data to the estimated body size.

7 Claims, 7 Drawing Sheets

(51) Int. Cl.
  *G01B 21/02* (2006.01)
  *G06T 7/73* (2017.01)

(56) References Cited

FOREIGN PATENT DOCUMENTS

| | | | | |
|---|---|---|---|---|
| JP | 2013217662 A | 10/2013 | | |
| JP | 2014186525 A | 10/2014 | | |
| JP | 2015061577 A | 4/2015 | | |
| JP | 2017146116 A | 8/2017 | | |
| JP | 2017176803 A | 10/2017 | | |
| WO | WO-2011028383 A1 * | 3/2011 | ............. | G06F 1/163 |
| WO | WO-2013058978 A1 * | 4/2013 | ........... | A61B 5/1079 |

OTHER PUBLICATIONS

International Search Report and Written Opinion dated May 22, 2018, from the corresponding PCT/JP2018,010459, 8 sheets.

\* cited by examiner

BODY SIZE ESTIMATION APPARATUS, BODY SIZE ESTIMATION METHOD, AND PROGRAM

TECHNICAL FIELD

The present invention relates to a body size estimation apparatus, a body size estimation method, and a program.

BACKGROUND ART

There has been known a body tracking technology that estimates, on the basis of data indicating the positions or directions of a plurality of trackers that a user wears, the posture of the user with IK (inverse kinematics), for example.

In such a body tracking technology, the accuracy of posture estimation can be enhanced with the use of data indicating the body size of a user such as the height. For example, the distinction of whether a petite user is in a posture with the spread arms and legs or a large user is in a posture with the bent arms and legs can be made.

Entertainment systems such as games have been configured to change, depending on a change in posture of a user that is estimated in this way, the shape or posture of an object, for example, a character model.

SUMMARY

Technical Problem

To estimate the body size of a user, the user has needed to take a posture with the arms stretched out (what is called a T-pose) in advance in the related art.

The present invention has been made in view of the above-mentioned problem, and it is one object of the present invention to provide a body size estimation apparatus, a body size estimation method, and a program that enable the estimation of the body size of a user even when the user has not taken a T-pose in advance.

Solution to Problem

In order to solve the above-mentioned problem, a body size estimation apparatus according to the present invention includes: a body size data storage unit configured to store body size data indicating a body size of a user; a position data acquisition unit configured to acquire position data indicating positions of a plurality of body parts away from each other of the user; a body size estimation unit configured to estimate a body size of the user based on the positions of the plurality of body parts indicated by the position data; and a body size update unit configured to update, in a case where the estimated body size is larger than the body size indicated by the body size data stored in the body size data storage unit, the body size data such that the body size data indicates the estimated body size.

In one aspect of the present invention, the body size estimation unit estimates the body size of the user based on a position of a head of the user and a position of a foot of the user that are indicated by the position data.

Alternatively, the body size data storage unit stores height data indicating a height of the user. The body size estimation unit estimates a height of the user based on a position of a head of the user and positions of hands of the user that are indicated by the position data. The body size update unit updates, in a case where the estimated height is greater than the height indicated by the height data stored in the body size data storage unit, the height data such that the height data indicates the estimated height.

In this aspect, the body size estimation unit may estimate positions of shoulders of the user based on the position of the head of the user indicated by the position data. The body size estimation unit may estimate each of arm lengths of the user based on the position of one of the hands of the user indicated by the position data and the estimated position of the shoulder corresponding to the hand. The body size estimation unit may estimate the height of the user based on the estimated arm lengths of the user.

Alternatively, the body size data storage unit stores height data indicating a height of the user and arm length data indicating arm lengths of the user. The body size estimation unit estimates a height of the user based on a position of a head of the user and a position of a foot of the user that are indicated by the position data. The body size estimation unit estimates positions of shoulders of the user based on the position of the head of the user indicated by the position data. The body size estimation unit estimates each of arm lengths of the user based on a position of one of hands of the user indicated by the position data and the estimated position of the shoulder corresponding to the hand. The body size update unit updates, in a case where the estimated height is greater than the height indicated by the height data stored in the body size data storage unit, the height data such that the height data indicates the estimated height. The body size update unit updates, in a case where the estimated arm lengths are greater than the arm lengths indicated by the arm length data stored in the body size data storage unit, the arm length data such that the arm length data indicates the estimated arm lengths.

Further, according to one aspect of the present invention, the acquisition by the position data acquisition unit, the estimation by the body size estimation unit, and the update by the body size update unit are repeatedly executed.

Further, another body size estimation apparatus according to the present invention includes: a position data acquisition unit configured to acquire position data indicating positions of a plurality of body parts away from each other of a user in an upright posture; an intermediate estimation unit configured to estimate arm lengths and a shoulder width of the user based on a position of a head of the user and positions of hands of the user that are indicated by the position data; and a body size estimation unit configured to estimate a body size of the user based on the estimated arm lengths and the estimated shoulder width of the user.

In one aspect of the present invention, the body size estimation unit estimates a horizontal body size of the user based on the estimated arm lengths and the estimated shoulder width of the user. The body size estimation unit estimates a height of the user based on the position of the head of the user and a position of a foot of the user that are indicated by the position data.

Alternatively, the body size estimation unit estimates a height of the user based on the estimated arm lengths and the estimated shoulder width of the user.

Further, in one aspect of the present invention, the body size estimation unit estimates the estimated shoulder width as an anteroposterior body size of the user.

Further, in one aspect of the present invention, the position data acquisition unit acquires the position data indicating a position that is measured by a tracker that the user wears or grasps.

Further, a body size estimation method according to the present invention includes the steps of: acquiring position data indicating positions of a plurality of body parts away from each other of a user; estimating a body size of the user based on the positions of the plurality of body parts indicated by the position data; and updating, in a case where the estimated body size is larger than a body size of the user indicated by body size data stored in a body size data storage unit configured to store the body size data indicating the body size, the body size data such that the body size data indicates the estimated body size.

Further, another body size estimation method according to the present invention includes the steps of: acquiring position data indicating positions of a plurality of body parts away from each other of a user in an upright posture; estimating arm lengths and a shoulder width of the user based on a position of a head of the user and positions of hands of the user that are indicated by the position data; and estimating a body size of the user based on the estimated arm lengths and the estimated shoulder width of the user.

Further, a program according to the present invention causes a computer to execute the procedures of: acquiring position data indicating positions of a plurality of body parts away from each other of a user; estimating a body size of the user based on the positions of the plurality of body parts indicated by the position data; updating, in a case where the estimated body size is larger than a body size of the user indicated by body size data stored in a body size data storage unit configured to store the body size data indicating the body size, the body size data such that the body size data indicates the estimated body size.

Further, another program according to the present invention causes a computer to execute the procedures of: acquiring position data indicating positions of a plurality of body parts away from each other of a user in an upright posture; estimating arm lengths and a shoulder width of the user based on a position of a head of the user and positions of hands of the user that are indicated by the position data; and estimating a body size of the user based on the estimated arm lengths and the estimated shoulder width of the user.

DESCRIPTION OF EMBODIMENTS

First Embodiment

Now, a first embodiment that is one embodiment of the present invention is described in detail with reference to the drawings.

Figure 1:
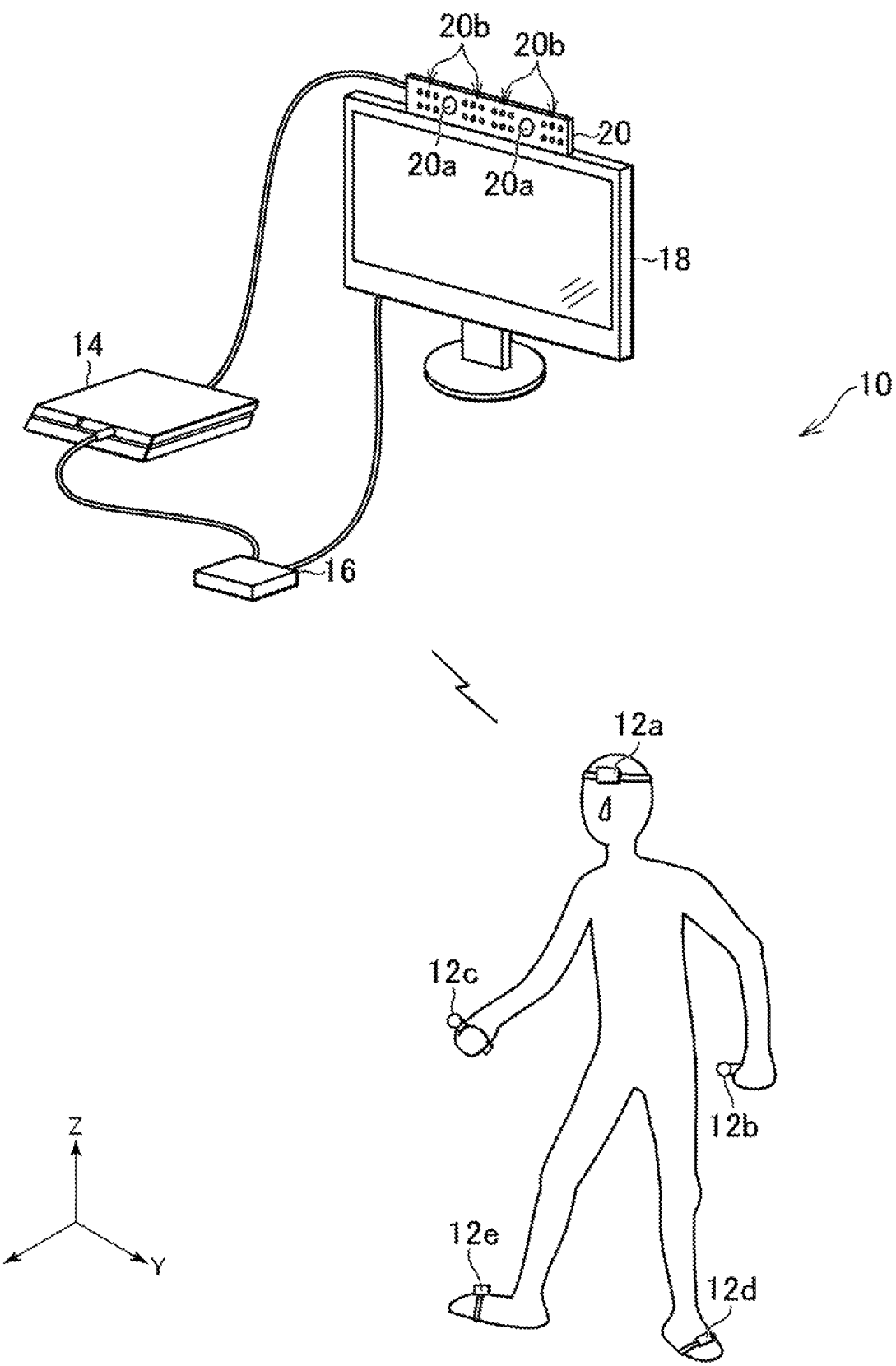
FIG. 1 is a configuration diagram illustrating an example of an entertainment system according to one embodiment of the present invention.
Figure 2:
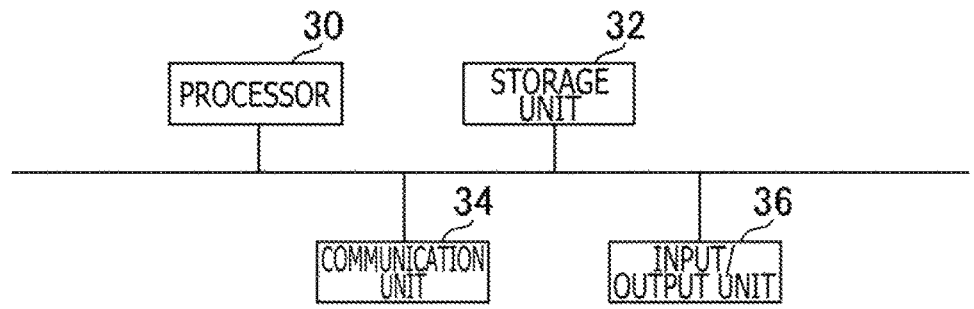
FIG. 2 is a configuration diagram illustrating an example of an entertainment apparatus according to one embodiment of the present invention.

FIG. 1 is a diagram illustrating an example of the configuration of an entertainment system 10 according to the first embodiment of the present invention. FIG. 2 is a diagram illustrating an example of the configuration of an entertainment apparatus 14 according to the present embodiment.

As illustrated in FIG. 1, the entertainment system 10 according to the present embodiment includes a plurality of trackers 12 (trackers 12a to 12e in the example in FIG. 1), the entertainment apparatus 14, a relay apparatus 16, a display 18, and a camera microphone unit 20.

The tracker 12 according to the present embodiment is a device configured to track, for example, the position and direction of the tracker 12. Here, the tracker 12 may include various sensors, for example, a camera, an inertial sensor (IMU), a geomagnetic sensor (azimuth sensor), an acceleration sensor, a motion sensor, and a GPS (Global Positioning System) module. Moreover, the tracker 12 may identify the position and direction of the tracker 12 on the basis of sensing data corresponding to the measurement results of the sensors of the tracker 12.

Further, for example, the position and direction of the tracker 12 may be identified on the basis of an image that includes the image of the tracker 12 and is taken by a camera 20a included in the camera microphone unit 20, which is described later.

In the present embodiment, the tracker 12a, the tracker 12b, the tracker 12c, the tracker 12d, and the tracker 12e are worn on the head, left hand, right hand, left foot, and right foot of a user, respectively. Here, as illustrated in FIG. 1, the user may grasp the tracker 12b and the tracker 12c with the hands. In the present embodiment, the position and direction identified by the tracker 12a, the position and direction identified by the tracker 12b, the position and direction identified by the tracker 12c, the position and direction identified by the tracker 12d, and the position and direction identified by the tracker 12e correspond to the position and direction of the user's head, the position and direction of the user's left hand, the position and direction of the user's right hand, the position and direction of the user's left foot, and the position and direction of the user's right foot, respectively. In this way, in the present embodiment, a plurality of the trackers 12 identify the positions and directions of a plurality of body parts of the user.

The entertainment apparatus 14 according to the present embodiment is a computer, for example, a game console, a DVD (Digital Versatile Disc) player, or a Blu-ray (registered trademark) player. The entertainment apparatus 14 according to the present embodiment generates video or sound by executing a game program or by reproducing content stored in the entertainment apparatus 14 or recorded on an optical disc, for example. Moreover, the entertainment apparatus 14 according to the present embodiment outputs a video signal indicating the generated video or a sound signal indicating the generated sound to the display 18 through the relay apparatus 16.

The entertainment apparatus 14 according to the present embodiment includes, for example, as illustrated in FIG. 2, a processor 30, a storage unit 32, a communication unit 34, and an input/output unit 36.

The processor 30 is, for example, a program control device such as a CPU (Central Processing Unit) configured to operate in accordance with a program installed on the entertainment apparatus 14. The processor 30 according to the present embodiment also includes a GPU (Graphics Processing Unit) configured to draw an image in a frame buffer on the basis of a graphics command or data supplied from the CPU.

The storage unit 32 is, for example, a storage element, such as a ROM (Read-Only Memory) or a RAM (Random Access Memory), or a hard disk drive. The storage unit 32 stores programs or the like that are executed by the processor 30. Further, the storage unit 32 according to the present embodiment has, secured therein, the area of the frame buffer in which the GPU draws images.

The communication unit 34 is, for example, a communication interface such as a wireless LAN (Local Area Network) module.

The input/output unit 36 is an input/output port such as an HDMI (registered trademark) (High-Definition Multimedia Interface) port or a USB (Universal Serial Bus) port.

The relay apparatus 16 according to the present embodiment is a computer configured to relay video signals or sound signals output from the entertainment apparatus 14, thereby outputting the video signals or sound signals to the display 18.

The display 18 according to the present embodiment is a liquid crystal display or the like, and displays, for example, a video indicated by a video signal output from the entertainment apparatus 14.

The camera microphone unit 20 according to the present embodiment includes, for example, the camera 20a configured to output the taken image of an object to the entertainment apparatus 14, and a microphone 20b configured to acquire the surrounding sound to convert the sound into sound data, and output the sound data to the entertainment apparatus 14. Further, the camera 20a according to the present embodiment is a stereo camera.

The tracker 12 and the relay apparatus 16 can transmit/receive data to/from each other wirelessly, for example. The entertainment apparatus 14 and the relay apparatus 16 are connected to each other through, for example, an HDMI cable or a USB cable, and can transmit/receive data to/from each other. The relay apparatus 16 and the display 18 are connected to each other through, for example, an HDMI cable. The entertainment apparatus 14 and the camera microphone unit 20 are connected to each other through, for example, an AUX (Auxiliary) cable.

Figure 3:
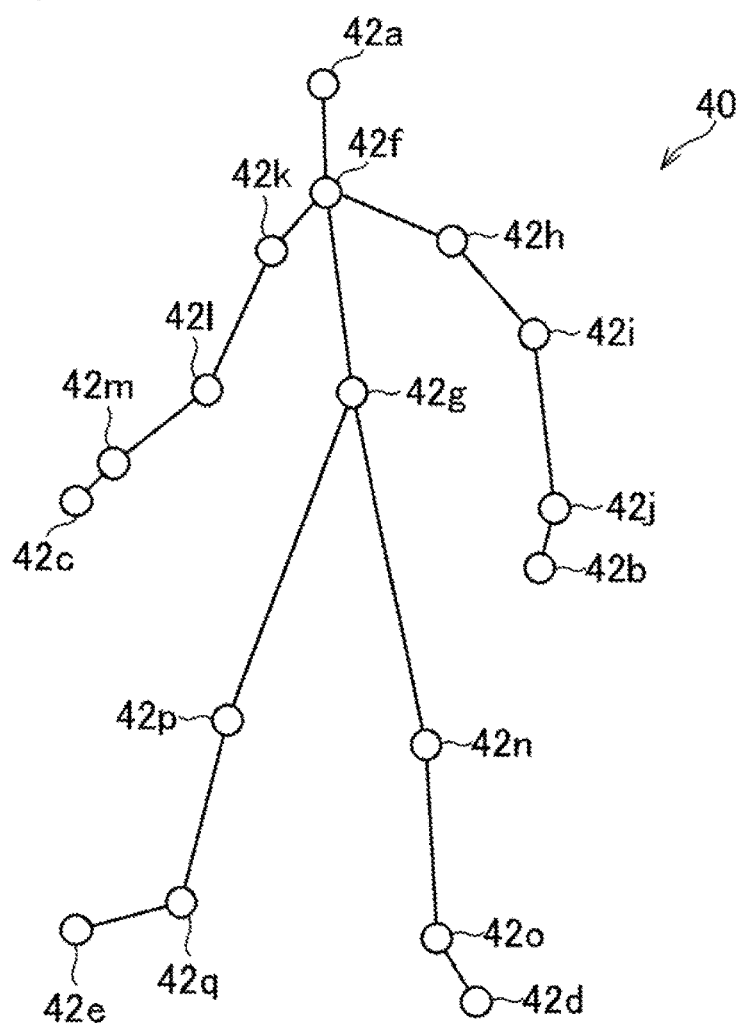
FIG. 3 is a diagram illustrating an example of a skeleton model.

In the present embodiment, for example, while the entertainment apparatus 14 is executing a game program, various types of processing such as game processing based on the positions or directions of a plurality of body parts of the user in a skeleton model 40 illustrated in FIG. 3 are executed. Then, a video based on the processing results is displayed on the display 18, for example.

As illustrated in FIG. 3, the skeleton model 40 according to the present embodiment includes a head node 42a, a left hand node 42b, a right hand node 42c, a left foot node 42d, and a right foot node 42e. The head node 42a corresponds to the user's head on which the tracker 12a is worn. The left hand node 42b corresponds to the user's left hand on which the tracker 12b is worn. The right hand node 42c corresponds to the user's right hand on which the tracker 12c is worn. The left foot node 42d corresponds to the user's left foot on which the tracker 12d is worn. The right foot node 42e corresponds to the user's right foot on which the tracker 12e is worn.

Further, the skeleton model 40 includes, in addition to the above-mentioned nodes 42, a chest node 42f, a waist node 42g, a left shoulder node 42h, a left elbow node 42i, and a left wrist node 42j. Further, the skeleton model 40 also includes a right shoulder node 42k, a right elbow node 42l, a right wrist node 42m, a left knee node 42n, a left ankle node 42o, a right knee node 42p, and a right ankle node 42q. As illustrated in FIG. 3, these nodes 42 are connected to each other by links.

These nodes 42 correspond to the respective body parts of the user. Moreover, in the present embodiment, body tracking based on, for example, the identified positions and directions of a plurality of the trackers 12 and body size data indicating the user's body size is performed. Here, for example, with inverse kinematics, with respect to each of a plurality of the nodes 42 included in the skeleton model 40, the estimation of a position relative to a reference position in the initial state and of a direction relative to a reference direction in the initial state is executed.

In the body tracking technology, the accuracy of posture estimation can be enhanced with the use of body size data indicating the body size of a user. For example, the distinction of whether a petite user is in a posture with the spread arms and legs or a large user is in a posture with the bent arms and legs can be made.

To estimate the body size of a user, the user has needed to take a posture with the arms stretched out (what is called a T-pose) in advance in the related art.

On the other hand, in the present embodiment, for example, when the user playing a game while wearing a plurality of the trackers 12 moves, the body size data is dynamically updated. Thus, in the present embodiment, in body size data generation, there is no need to execute calibration that requires the user to take a T-pose in advance (for example, before the user starts playing the game).

Now, the functions of the entertainment apparatus 14 and processing that is executed in the entertainment apparatus 14 in terms of body size data dynamic update in the present embodiment are described.

Figure 4:
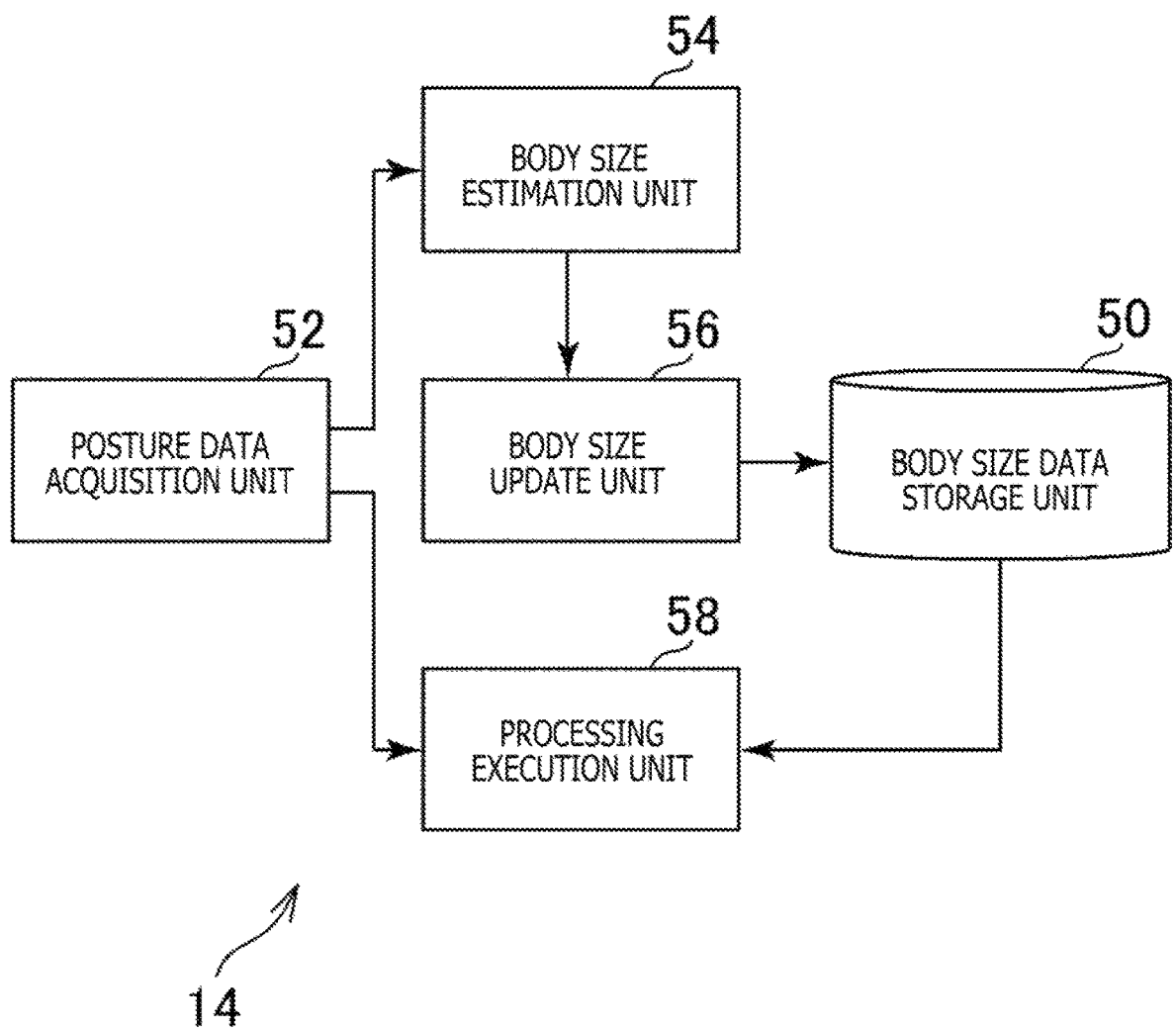
FIG. 4 is a functional block diagram illustrating examples of functions that are implemented in an entertainment apparatus according to a first embodiment of the present invention.

FIG. 4 is a functional block diagram illustrating examples of functions that are implemented in the entertainment apparatus 14 according to the present embodiment. Note that, the entertainment apparatus 14 according to the present embodiment is not necessarily has, implemented therein, all the functions illustrated in FIG. 4, and may have, implemented therein, functions other than the functions illustrated in FIG. 4.

As illustrated in FIG. 4, the entertainment apparatus 14 according to the present embodiment functionally includes, for example, a body size data storage unit 50, a posture data acquisition unit 52, a body size estimation unit 54, a body size update unit 56, and a processing execution unit 58.

The body size data storage unit 50 is implemented with the storage unit 32 being a main component. The posture data acquisition unit 52 is implemented with the processor 30 and the input/output unit 36 being main components. The body size estimation unit 54, the body size update unit 56, and the processing execution unit 58 are each implemented with the processor 30 being a main component. The entertainment apparatus 14 according to the present embodiment plays the role of a body size estimation apparatus configured to estimate the user's body size.

The above-mentioned functions may be implemented by the processor 30 executing programs installed on the entertainment apparatus 14 that is a computer, the programs including commands corresponding to the above-mentioned functions. For example, the programs may be supplied to the entertainment apparatus 14 through a computer-readable information storage medium such as an optical disc, a magnetic disk, a magnetic tape, a magneto-optical disk, or a flash memory, or through the Internet or the like.

In the present embodiment, the body size data storage unit 50 stores, for example, body size data indicating the user's body size. Here, for example, as the initial value of the body size data, a predetermined value may be set. Alternatively, as the initial value of the body size data, a value based on the user's age may be set. As described later, the body size data is updated so that a body size indicated by the body size data is gradually increased. Thus, as the initial value of the body size data, a value slightly smaller than a value indicating an average user body size is desirably set.

Note that, the body size data storage unit 50 may store height data indicating the user's height. Further, the body size data storage unit 50 may store arm length data indicating the user's arm lengths. Further, the body size data storage unit 50 may store horizontal body size data indicating the user's horizontal body size.

In the present embodiment, the posture data acquisition unit 52 acquires, for example, position data indicating the positions of a plurality of the body parts away from each other of the user. Here, the posture data acquisition unit 52 may acquire posture data indicating positions and directions measured at a predetermined sampling rate by the trackers 12a to 12e that the user wears or grasps as described above.

In the present embodiment, the body size estimation unit 54 estimates, for example, the user's body size on the basis of the positions of a plurality of the body parts indicated by posture data acquired by the posture data acquisition unit 52.

Here, the body size estimation unit 54 may estimate the user's body size (for example, the body size in the height direction, namely, the height) on the basis of the position of the user's head and the positions of the user's feet that are indicated by the position data. For example, the user's height may be estimated on the basis of the position of the tracker 12a and the position of the tracker 12d. Further, for example, the user's height may be estimated on the basis of the position of the tracker 12a and the position of the tracker 12e.

Further, the body size estimation unit 54 may estimate the user's arm length on the basis of the position of the user's hand indicated by the position data and the estimated position of the shoulder corresponding to the hand. Moreover, the body size estimation unit 54 may estimate the user's body size (for example, the horizontal body size) on the basis of a position indicated by posture data that the posture data acquisition unit 52 acquires and the positions of the shoulders that the body size estimation unit 54 estimates. For example, the user's horizontal body size may be estimated on the basis of the position of the tracker 12b and the estimated position of the left shoulder. Further, for example, the user's horizontal body size may be estimated on the basis of the position of the tracker 12c and the estimated position of the right shoulder.

Further, the body size estimation unit 54 may estimate the user's height on the basis of the position of the user's head and the positions of the user's hands that are indicated by the position data. Here, for example, the user's height may be estimated on the basis of the user's arm lengths estimated as described above.

In the present embodiment, the body size update unit 56 updates, for example, in a case where an estimated body size is larger than the body size indicated by the body size data stored in the body size data storage unit 50, the body size data so that the body size data indicates the estimated body size.

Here, the body size update unit 56 may update, in a case where an estimated height is greater than the height indicated by the height data stored in the body size data storage unit 50, the height data so that the height data indicates the estimated height. Further, the body size update unit 56 may update, in a case where estimated arm lengths are greater than the arm lengths indicated by the arm length data stored in the body size data storage unit 50, the arm length data so that the arm length data indicates the estimated arm lengths.

In the present embodiment, the processing execution unit 58 executes, for example, the body tracking processing on the basis of the body size indicated by the body size data stored in the body size data storage unit 50 and positions and directions indicated by posture data that the posture data acquisition unit 52 acquires. Moreover, the processing execution unit 58 executes, on the basis of the execution result of the body tracking processing, various types of processing such as the processing of changing the shape or posture of a character model.

Figure 5:
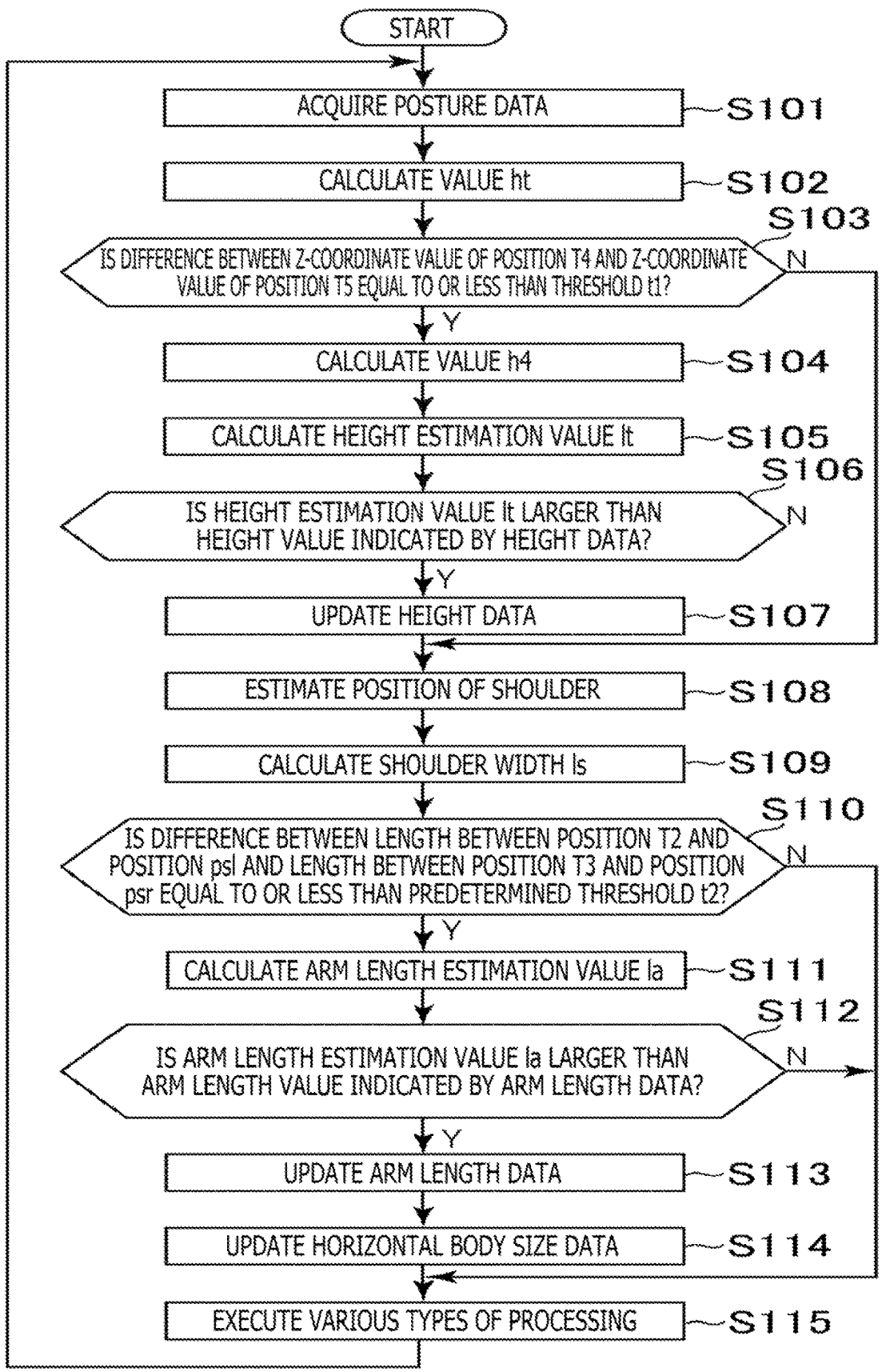
FIG. 5 is a flow chart illustrating an example of the flow of processing that is performed in the entertainment apparatus according to the first embodiment of the present invention.
Figure 6:
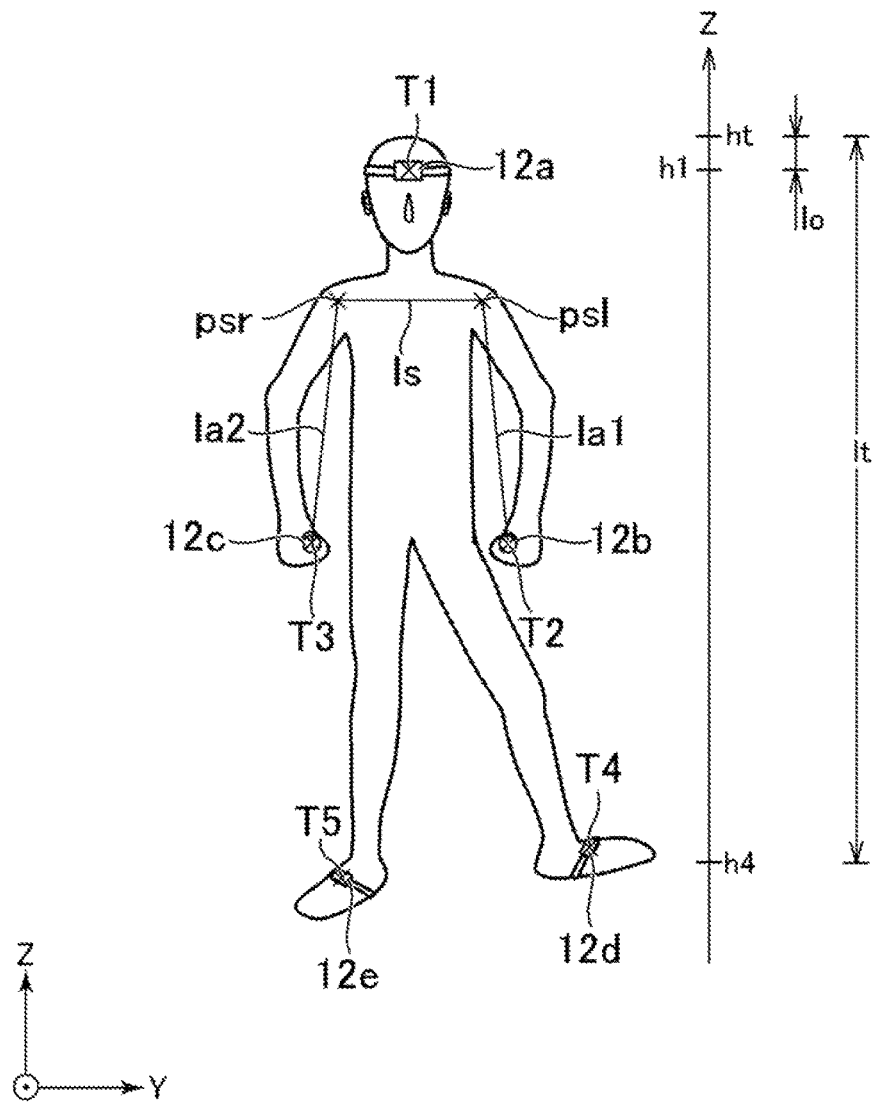
FIG. 6 is a schematic diagram illustrating an example of a user playing a game.

Here, an example of the flow of processing that is performed in the entertainment apparatus 14 according to the present embodiment is described with reference to the flow chart of FIG. 5 and the schematic diagram of FIG. 6. FIG. 6 is a schematic diagram illustrating an example of the user playing a game. In the present processing example, the processing illustrated in S101 to S115, which are described below, is repeatedly executed at a predetermined sampling rate. Further, in the following description, the user's anteroposterior direction is the X-axis direction, the horizontal direction is the Y-axis direction, and the height direction is the Z-axis direction.

First, the posture data acquisition unit 52 acquires posture data indicating the positions and directions of the trackers 12a to 12e (S101). Here, in the following description, as illustrated in FIG. 6, the position of the tracker 12a, the position of the tracker 12b, the position of the tracker 12c, the position of the tracker 12d, and the position of the tracker 12e are denoted by T1, T2, T3, T4, and T5, respectively.

Then, the body size estimation unit 54 calculates, as a Z-coordinate value ht of the vertex, a value in which a predetermined offset value lo is added to a Z-coordinate value h1 of the position T1 (S102).

Then, the body size estimation unit 54 confirms whether or not a difference between the Z-coordinate value of the position T4 and the Z-coordinate value of the position T5 is equal to or less than a predetermined threshold t1 (S103).

In a case where it has been confirmed that the difference between the Z-coordinate value of the position T4 and the Z-coordinate value of the position T5 is equal to or less than the threshold t1 (S103: Y), the body size estimation unit 54 calculates a Z-coordinate value h4 that is the average value of the Z-coordinate value of the position T4 and the Z-coordinate value of the position T5 (S104).

Then, the body size estimation unit 54 calculates, as an estimation value lt of the height, a difference between the Z-coordinate value ht of the vertex calculated in the processing illustrated in S102 and the Z-coordinate value h4 calculated in the processing illustrated in S104 (S105).

Then, the body size update unit 56 confirms whether or not the estimation value lt of the body size calculated in the processing illustrated in S105 is larger than the height value indicated by the height data stored in the body size data storage unit 50 (S106).

It is assumed that it has been confirmed that the value lt is larger than the height value indicated by the height data stored in the body size data storage unit 50 (S106: Y). In this case, the body size update unit 56 updates the height data stored in the body size data storage unit 50 so that the height data indicates the estimation value lt of the body size calculated in the processing illustrated in S105 (S107).

Then, the body size estimation unit 54 estimates the positions of the user's shoulders (S108). Here, for example, a predetermined offset value psro may be added to the value indicating the position T1 to estimate a value indicating a position psr of the right shoulder. Further, for example, another predetermined offset value pslo may be added to the value indicating the position T1 to estimate a value indicating a position psl of the left shoulder. Note that, also in a case where it has been confirmed in the processing illustrated in S103 that the difference between the Z-coordinate value of the position T4 and the Z-coordinate value of the position T5 is not equal to or less than the threshold t1 (S103: N), the processing illustrated in S108 is executed. In this case, the value indicating the position T4 and the value indicating the position T5 are highly possibly abnormal values based on the error, and accordingly the processing illustrated in S104 to S107 is skipped. Further, also in a case where it has been confirmed in the processing illustrated in S106 that the value lt is not larger than the height value indicated by the height data stored in the body size data storage unit 50 (S106: N), the processing illustrated in S108 is executed.

Then, the body size estimation unit 54 calculates, as a shoulder width ls, a distance between the position psr of the right shoulder and the position psl of the left shoulder estimated in the processing illustrated in S108 (S109).

Then, the body size estimation unit 54 confirms whether or not a difference between a distance between the position T2 and the position psl and a distance between the position T3 and the position psr is equal to or less than a predetermined threshold t2 (S110).

It is assumed that it has been confirmed that the difference between a length la1 between the position T2 and the position psl and a length la2 between the position T3 and the position psr is equal to or less than the predetermined threshold t2 (S110: Y). In this case, the body size estimation unit 54 calculates, as an estimation value la of the arm lengths, the average value of the value indicating the length la1 between the position T2 and the position psr and the value indicating the length la2 between the position T3 and the position psl (S111).

Then, the body size update unit 56 confirms whether or not the estimation value la calculated in the processing illustrated in S111 is larger than the arm length value indicated by the arm length data stored in the body size data storage unit 50 (S112).

It is assumed that it has been confirmed that the value la is larger than the value of the arm length data stored in the body size data storage unit 50 (S112: Y). In this case, the body size update unit 56 updates the arm length data stored in the body size data storage unit 50 so that the arm length data indicates the estimation value la of the arm lengths calculated in the processing illustrated in S111 (S113).

Then, the body size estimation unit 54 updates the horizontal body size data stored in the body size data storage unit 50 so that the horizontal body size data indicates the sum of a value twice as large as the value of the arm length data and the value of the shoulder width is described above (S114).

Then, the processing execution unit 58 executes various types of processing such as the body tracking processing on the basis of the height indicated by the height body size data, the horizontal body size indicated by the horizontal body size data, and the positions and directions indicated by the posture data acquired in the processing illustrated in S101 (S115). Note that, also in a case where it has been confirmed in the processing illustrated in S110 that the difference between the distance between the position T2 and the position psl and the distance between the position T3 and the position psr is not equal to or less than the predetermined threshold t2 (S110: N), the processing illustrated in S115 is executed. In this case, the value indicating the position T2 and the value indicating the position T3 are highly possibly abnormal values based on the error, and accordingly the processing illustrated in S111 to S114 is skipped. Further, also in a case where it has been confirmed in the processing illustrated in S112 that the value la is not larger than the arm length value indicated by the arm length data stored in the body size data storage unit 50 (S112: N), the processing illustrated in S115 is executed.

Then, the processing returns to the processing illustrated in S101.

Note that, in the above description, the user's body size is estimated on the basis of the positions of the five parts away from each other, but the user's body size can be estimated with the positions of at least two parts. For example, the user's body size may be estimated on the basis of the position T1 and the position T4. Further, for example, the user's body size may be estimated on the basis of the position T1 and the position T5. Further, for example, the user's body size may be estimated on the basis of the position T2 and the position T3.

It has been known that the horizontal body size of a human is substantially the same as the height. In consideration of this, the estimation value of the horizontal body size may be used as the height estimation value as described above. For example, in the processing example illustrated in FIG. 5, the height data stored in the body size data storage unit 50 may be updated so that the height data indicates the sum of the value twice as large as the value of the arm length data and the value of the shoulder width is described above. In this case, the user's height can be estimated with the tracker 12 worn on the head and the trackers 12 worn on or grasped by the hands. This means that there is no need for the user to wear the trackers 12 on the feet. Further, for example, the height estimation value may be used as the estimation value of the horizontal body size.

Second Embodiment

Now, a second embodiment that is another embodiment of the present invention is described.

An example of the configuration of the entertainment system 10 according to the second embodiment is similar to the one illustrated in FIG. 1, and hence a description thereof is omitted. An example of the configuration of the entertainment apparatus 14 according to the second embodiment is similar to the one illustrated in FIG. 2, and hence a description thereof is omitted.

In the second embodiment, with the user being in an upright posture, the user's body size is estimated. Here, for example, the above-mentioned body size data is generated. Also in the second embodiment, there is no need for the user to take the T-pose in advance to generate body size data.

Figure 7:
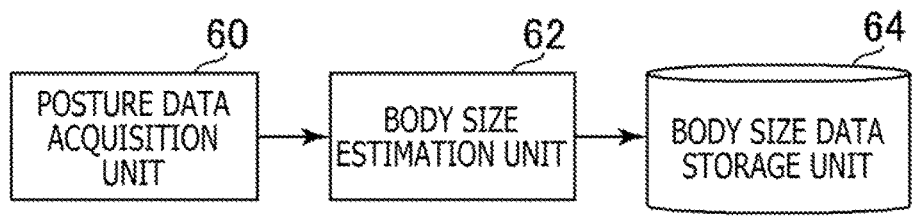
FIG. 7 is a functional block diagram illustrating examples of functions that are implemented in an entertainment apparatus according to a second embodiment of the present invention.

FIG. 7 is a functional block diagram illustrating examples of functions that are implemented in the entertainment apparatus 14 according to the present embodiment. Note that, the entertainment apparatus 14 according to the present embodiment is not necessarily has, implemented therein, all the functions illustrated in FIG. 7, and may have, implemented therein, functions other than the functions illustrated in FIG. 7.

As illustrated in FIG. 7, the entertainment apparatus 14 according to the present embodiment functionally includes, for example, a posture data acquisition unit 60, a body size estimation unit 62, and a body size data storage unit 64.

The posture data acquisition unit 60 is implemented with the processor 30 and the input/output unit 36 being main components. The body size estimation unit 62 is implemented with the processor 30 being a main component. The body size data storage unit 64 is implemented with the storage unit 32 being a main component. The entertainment apparatus 14 according to the present embodiment plays the role of a body size estimation apparatus configured to estimate the user's body size.

The above-mentioned functions may be implemented by the processor 30 executing programs installed on the entertainment apparatus 14 that is a computer, the programs including commands corresponding to the above-mentioned functions. For example, the programs may be supplied to the entertainment apparatus 14 through a computer-readable information storage medium such as an optical disc, a magnetic disk, a magnetic tape, a magneto-optical disk, or a flash memory, or through the Internet or the like.

In the present embodiment, the posture data acquisition unit 60 acquires, for example, position data indicating the positions of a plurality of the body parts away from each other of the user in the upright posture. Here, the posture data acquisition unit 60 may acquire posture data indicating positions and directions measured at a predetermined sampling rate by the trackers 12a to 12e that the user wears or grasps as described above.

In the present embodiment, the body size estimation unit 62 estimates, for example, the user's arm lengths and the user's shoulder width on the basis of the position of the user's head and the positions of the user's hands that are indicated by the position data. For example, the user's arm lengths and the user's shoulder width may be estimated on the basis of the position of the tracker 12a, the position of the tracker 12b, and the position of the tracker 12c. Moreover, the body size estimation unit 62 estimates the user's body size on the basis of the estimated user's arm lengths and the estimated user's shoulder width. Further, in the present embodiment, the body size estimation unit 62 generates body size data indicating the estimated user's body size.

Here, the body size estimation unit 62 may estimate the user's horizontal body size on the basis of the estimated user's arm lengths and the estimated user's shoulder width. Further, the body size estimation unit 62 may estimate the user's height on the basis of the position of the user's head and the positions of the user's feet that are indicated by the position data.

Further, the body size estimation unit 62 may estimate the user's height on the basis of the estimated user's arm lengths and the estimated user's shoulder width.

Further, since the shoulder width of a human is considered to be substantially the same as the anteroposterior body size, the body size estimation unit 62 may estimate the estimated shoulder width as the user's anteroposterior body size.

In the present embodiment, the body size data storage unit 64 stores, for example, body size data generated by the body size estimation unit 62. The body size data indicates the user's body size.

Moreover, in the present embodiment, for example, processing such as body tracking using the body size indicated by the body size data stored in the body size data storage unit 64 may be executed. For example, with inverse kinematics, with respect to each of a plurality of the nodes 42 included in the skeleton model 40 illustrated in FIG. 3, the estimation of a position relative to a reference position in the initial state and of a direction relative to a reference direction in the initial state may be executed. Further, on the basis of the execution results of the body tracking processing, various types of processing such as the processing of changing the shape or posture of a character model may be executed.

Figure 8:
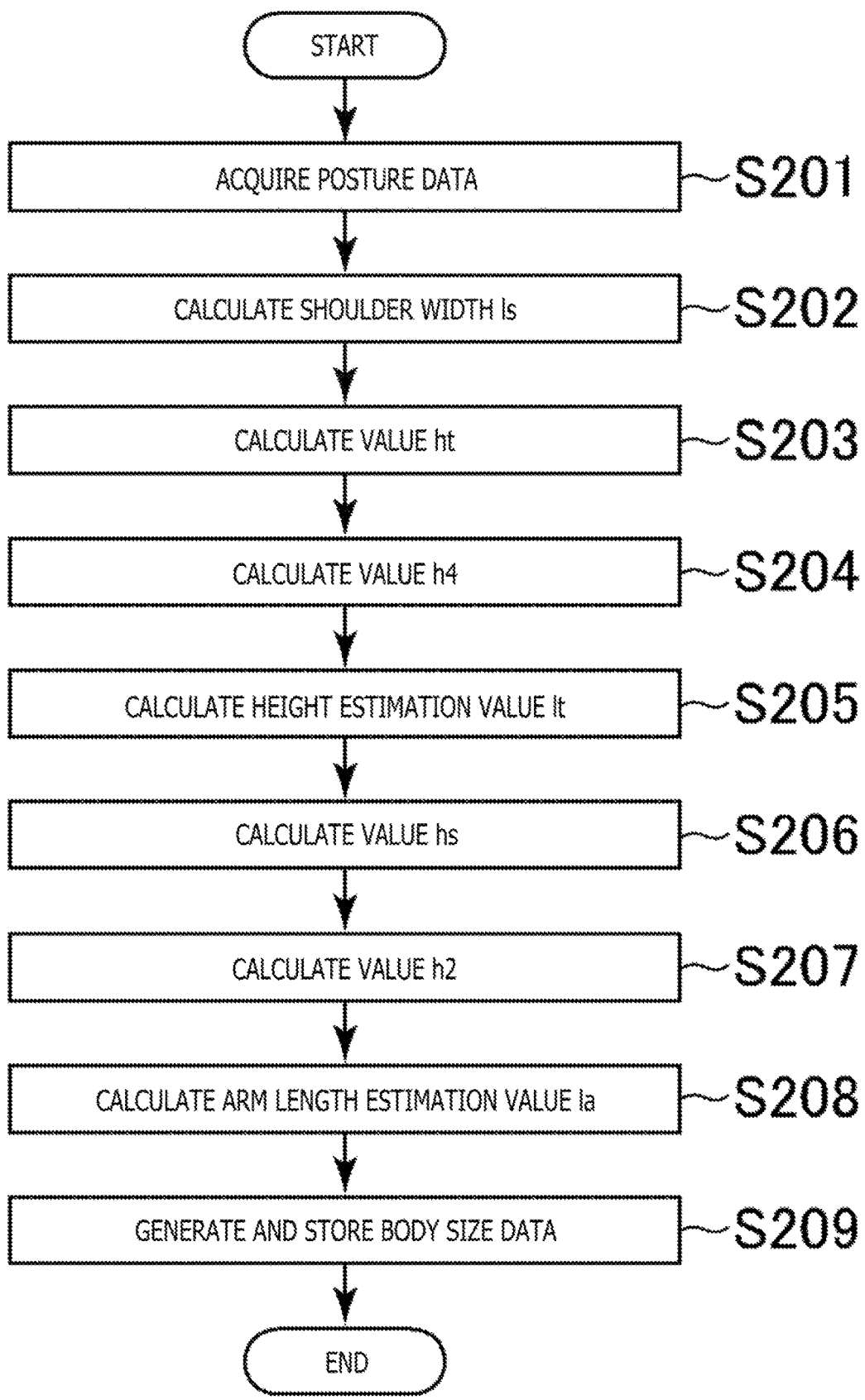
FIG. 8 is a flow chart illustrating an example of the flow of processing that is performed in the entertainment apparatus according to the second embodiment of the present invention.

Here, an example of the flow of processing that is performed in the entertainment apparatus 14 according to the present embodiment is described with reference to the flow chart of FIG. 8 and the schematic diagram of FIG. 9.

Figure 9:
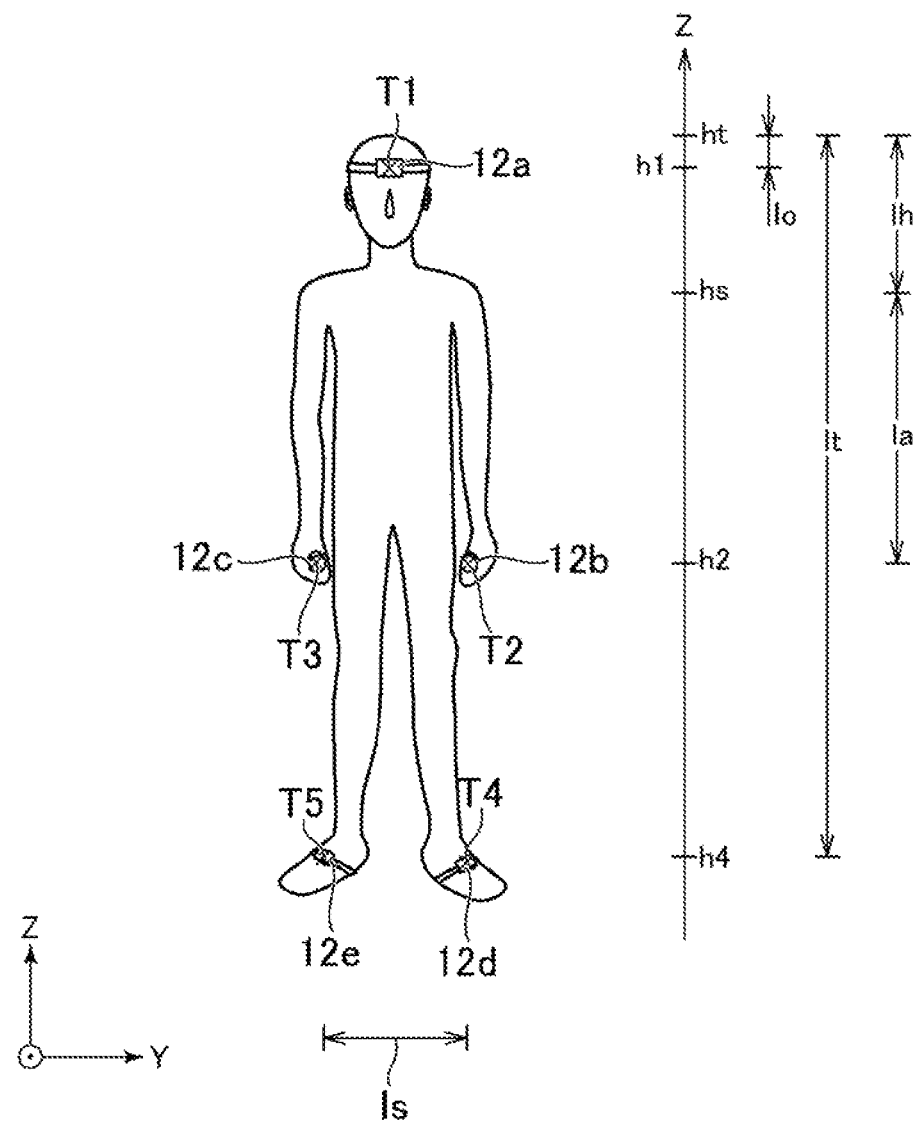
FIG. 9 is a schematic diagram illustrating an example of the user in an upright posture.

FIG. 9 is a schematic diagram illustrating an example of the user in the upright posture. In the following description, the user's anteroposterior direction is the X-axis direction, the horizontal direction is the Y-axis direction, and the height direction is the Z-axis direction.

First, the posture data acquisition unit 60 acquires posture data indicating the positions and directions of the trackers 12a to 12e when the user is in the upright posture (S201). Here, in the following description, as illustrated in FIG. 8, the position of the tracker 12a, the position of the tracker 12b, the position of the tracker 12c, the position of the tracker 12d, and the position of the tracker 12e are denoted by T1, T2, T3, T4, and T5, respectively.

Then, the body size estimation unit 62 calculates, as the shoulder width ls, a distance between the position T2 and the position T3 (S202).

Then, the body size estimation unit 62 calculates, as the Z-coordinate value ht of the vertex, a value in which the predetermined offset value lo is added to the Z-coordinate value h1 of the position T1 (S203).

Then, the body size estimation unit 62 calculates the Z-coordinate value h4 that is the average value of the Z-coordinate value of the position T4 and the Z-coordinate value of the position T5 (S204).

Then, the body size estimation unit 62 calculates, as the estimation value lt of the height, a difference between the Z-coordinate value ht of the vertex calculated in the processing illustrated in S203 and the Z-coordinate value h4 calculated in the processing illustrated S204 (S205).

Then, the body size estimation unit 62 subtracts a predetermined head length lh from the Z-coordinate value ht of the vertex to calculate a Z-coordinate value hs of the shoulders (S206).

Then, the body size estimation unit 62 calculates a Z-coordinate value h2 that is the average value of the Z-coordinate value of the position T2 and the Z-coordinate value of the position T3 (S207).

Then, the body size estimation unit 62 subtracts the Z-coordinate value h2 from the Z-coordinate value hs of the shoulders to calculate the estimation value la of the arm lengths (S208).

Then, the body size estimation unit 62 generates body size data, and the body size data storage unit 64 stores the body size data (S209). Here, the body size data may include anteroposterior body size data indicating the anteroposterior body size, horizontal body size data indicating the horizontal body size, and height data indicating the height. Moreover, as the value of the anteroposterior body size data, the value indicating the above-mentioned shoulder width ls may be set. Further, as the value of the horizontal body size data, a value obtained by adding the value indicating the shoulder width ls to a value twice as large as the arm length value la may be set. Further, as the value of the height data, the estimation value lt calculated in the processing illustrated in S205 may be set.

Note that, in the second embodiment, all the height, anteroposterior body size, and horizontal body size are not necessarily estimated.

Further, it has been known that the horizontal body size of a human is substantially the same as the height. In consideration of this, the estimation value of the horizontal body size may be used as the height estimation value as described above. For example, in the processing illustrated in S209 described above, the value obtained by adding the value indicating the shoulder width ls to the value twice as large as the arm length value la may be set as the value of the height data. In this case, the user's height can be estimated with the tracker 12 worn on the head and the trackers 12 worn on or grasped by the hands. This means that there is no need for the user to wear the trackers 12 on the feet.

Further, for example, the height estimation value may be handled as the estimation value of the horizontal body size.

Note that, the present invention is not limited to the above-mentioned embodiments.

For example, the tracker 12a may be an HMD (head-mounted display). In this case, on the display unit of the HMD, for example, there may be displayed a video based on the results of various types of processing such as game processing based on the positions or directions of a plurality of parts of the user.

Further, for example, part or all of the functions illustrated in FIG. 4 and FIG. 7 may be implemented by the tracker 12.

Further, the specific character strings and numerical values described above and the specific character strings and numerical values in the drawings are exemplary, and the present invention is not limited to these character strings and numerical values.

The invention claimed is:

1. A body size estimation apparatus, comprising:
a body size data storage unit configured to store body size data indicating a body size of a user;
a position data acquisition unit configured to acquire position data indicating positions of a plurality of body parts away from each other of the user when the user is in motion in view of the body size estimation apparatus,
wherein each of the plurality of body party comprises a marker worn on the user;
a body size estimation unit configured to estimate a body size of the user based on the positions of the plurality of body parts indicated by the position data; and
a body size update unit configured to update, in a case where the estimated body size is larger than the body size indicated by the body size data stored in the body size data storage unit, the body size data such that the body size data indicates the estimated body size,
wherein the body size data storage unit stores height data indicating a height of the user and arm length data indicating arm lengths of the user,
wherein, at predetermined intervals, the body size estimation unit estimates a height of the user based on a position of a head of the user and a position of a foot of the user that are indicated by the position data,
wherein, at the predetermined intervals, the body size estimation unit estimates positions of shoulders of the user based on the position of the head of the user indicated by the position data,
wherein, at the predetermined intervals, the body size estimation unit estimates each of arm lengths of the user based on a position of one of hands of the user indicated by the position data and the estimated position of the shoulder corresponding to the hand,
wherein the body size update unit updates, each time the estimated height is greater than the height indicated by the height data stored in the body size data storage unit, the height data such that the height data indicates the estimated height, and
the body size update unit updates, each time the estimated arm lengths are greater than the arm lengths indicated by the arm length data stored in the body size data storage unit, the arm length data such that the arm length data indicates the estimated arm lengths.

2. The body size estimation apparatus according to claim 1, wherein the acquisition by the position data acquisition unit, the estimation by the body size estimation unit, and the update by the body size update unit are repeatedly executed at the predetermined intervals while the user is in motion.

3. The body size estimation apparatus according to claim 1, wherein
the position data acquisition unit acquires the position data indicating a position that is measured by a tracker that the user wears or grasps.

4. A body size estimation apparatus, comprising:
a position data acquisition unit configured to acquire position data indicating positions of a plurality of body parts away from each other of a user when the user is in motion in view of the body size estimation apparatus in an upright posture;
an intermediate estimation unit configured to estimate, at predetermined intervals, arm lengths and a shoulder width of the user based on a position of a head of the user and positions of hands of the user that are indicated by the position data; and
a body size estimation unit configured to update a body size of the user based on the estimated arm lengths and the estimated shoulder width of the user every time a newly determined body size is greater than a previously determined body size;
wherein the body size estimation unit estimates a horizontal body size of the user based on the estimated arm lengths and the estimated shoulder width of the user,
wherein the body size estimation unit estimates a height of the user based on the position of the head of the user and a position of a foot of the user that are indicated by the position data, and
wherein the body size estimation unit estimates a height of the user based on the estimated arm lengths and the estimated shoulder width of the user.

5. The body size estimation apparatus according to claim 4, wherein
the body size estimation unit estimates the estimated shoulder width as an anteroposterior body size of the user.

6. A body size estimation method, comprising:
acquiring position data indicating positions of a plurality of body parts away from each other of the user when the user is in motion,
wherein each of the plurality of body party comprises a marker worn on the user;
estimating a body size of the user based on the positions of the plurality of body parts indicated by the position data;

updating, in a case where the estimated body size is larger than the body size indicated by the body size data stored in the body size data storage unit, the body size data such that the body size data indicates the estimated body size;

storing, height data indicating a height of the user and arm length data indicating arm lengths of the user;

estimating, at predetermined intervals, the height of the user based on a position of a head of the user and a position of a foot of the user that are indicated by the position data;

estimating, at the predetermined intervals, positions of shoulders of the user based on the position of the head of the user indicated by the position data;

estimating, at the predetermined intervals, each of arm lengths of the user based on a position of one of hands of the user indicated by the position data and the estimated position of the shoulder corresponding to the hand;

updating, each time the estimated height is greater than the height indicated by the stored height data, the height data such that the height data indicates the estimated height; and updating, each time the estimated arm lengths are greater than the arm lengths indicated by the stored arm length data, the arm length data such that the arm length data indicates the estimated arm lengths.

7. A non-transitory computer readable medium having stored thereon a program for a computer, comprising:

acquiring position data indicating positions of a plurality of body parts away from each other of the user when the user is in motion, wherein each of the plurality of body party comprises a marker worn on the user;

estimating a body size of the user based on the positions of the plurality of body parts indicated by the position data;

updating, in a case where the estimated body size is larger than the body size indicated by the body size data stored in the body size data storage unit, the body size data such that the body size data indicates the estimated body size;

storing, height data indicating a height of the user and arm length data indicating arm lengths of the user;

estimating, at predetermined intervals, the height of the user based on a position of a head of the user and a position of a foot of the user that are indicated by the position data;

estimating, at the predetermined intervals, positions of shoulders of the user based on the position of the head of the user indicated by the position data;

estimating, at the predetermined intervals, each of arm lengths of the user based on a position of one of hands of the user indicated by the position data and the estimated position of the shoulder corresponding to the hand;

updating, each time the estimated height is greater than the height indicated by the stored height data, the height data such that the height data indicates the estimated height; and updating, each time the estimated arm lengths are greater than the arm lengths indicated by the stored arm length data, the arm length data such that the arm length data indicates the estimated arm lengths.

\* \* \* \* \*